US008951748B2

(12) United States Patent
Roscoe et al.

(10) Patent No.: US 8,951,748 B2
(45) Date of Patent: Feb. 10, 2015

(54) RAPID DETECTION OF MOLDS THAT PRODUCE GLUCOSE OXIDASE

(75) Inventors: Stephen B. Roscoe, Woodbury, MN (US); Michael J. Svarovsky, Eagan, MN (US); Stephanie J. Moeller, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/515,856

(22) PCT Filed: Dec. 21, 2010

(86) PCT No.: PCT/US2010/061552
§ 371 (c)(1),
(2), (4) Date: Jun. 14, 2012

(87) PCT Pub. No.: WO2011/090662
PCT Pub. Date: Jul. 28, 2011

(65) Prior Publication Data
US 2012/0301911 A1 Nov. 29, 2012

Related U.S. Application Data

(60) Provisional application No. 61/291,144, filed on Dec. 30, 2009.

(51) Int. Cl.
*G01N 33/573* (2006.01)
*C12Q 1/04* (2006.01)
*C12Q 1/26* (2006.01)
*C12Q 1/54* (2006.01)

(52) U.S. Cl.
CPC ........ *C12Q 1/04* (2013.01); *C12Q 1/045* (2013.01); *C12Q 1/26* (2013.01); *C12Q 1/54* (2013.01)
USPC ............ 435/7.4; 435/4; 435/21; 435/32; 435/34

(58) Field of Classification Search
USPC ................. 435/4, 7.4, 21, 32, 341
See application file for complete search history.

(56) References Cited

U.S. PATENT DOCUMENTS

| | | | |
|---|---|---|---|
| 4,565,783 A | 1/1986 | Hansen | |
| 4,568,638 A | 2/1986 | Horwath | |
| 4,576,817 A * | 3/1986 | Montgomery et al. | 424/94.4 |
| 4,940,660 A * | 7/1990 | Hirai et al. | 435/7.92 |
| 5,089,413 A | 2/1992 | Nelson | |
| 5,364,767 A * | 11/1994 | Flowers et al. | 435/39 |
| 5,403,722 A | 4/1995 | Floeder | |
| 5,494,823 A | 2/1996 | Takemoto et al. | |
| RE35,286 E | 6/1996 | Nelson | |
| 5,601,998 A | 2/1997 | Mach | |
| 5,681,712 A | 10/1997 | Nelson | |
| 5,869,321 A * | 2/1999 | Franklin | 435/253.6 |
| 5,879,635 A | 3/1999 | Nason | |
| 6,002,789 A | 12/1999 | Olsztyn | |
| 6,243,286 B1 | 6/2001 | Kumagai | |
| 6,638,755 B1 | 10/2003 | Mizuochi et al. | |
| 7,141,387 B2 | 11/2006 | Ushiyama | |
| 7,223,364 B1 | 5/2007 | Johnston | |
| 7,298,885 B2 | 11/2007 | Green | |
| 7,298,886 B2 | 11/2007 | Plumb | |
| 7,560,234 B2 | 7/2009 | Dobson | |
| 7,691,601 B2 | 4/2010 | Orenga | |
| 2003/0032007 A1 | 2/2003 | Snaidr | |
| 2005/0136446 A1 | 6/2005 | Snaidr | |
| 2005/0196825 A1 * | 9/2005 | Roth et al. | 435/34 |
| 2006/0019306 A1 * | 1/2006 | Dobson et al. | 435/6 |
| 2009/0170144 A1 | 7/2009 | Heineman | |

FOREIGN PATENT DOCUMENTS

| | | |
|---|---|---|
| EP | 0 125 698 | 11/1984 |
| EP | 0930368 | 7/1999 |
| JP | 57-502200 | 12/1982 |
| JP | 6-181741 | 7/1994 |
| JP | 2000-325072 | 11/2000 |
| WO | 82/02563 | 8/1982 |

OTHER PUBLICATIONS

Wong et al. "Glucose oxidase: natural occurrence, function, properties and industrial applications." (2008) Applied Microbiology and Biotechnology, vol. 78: 927-938.*
Guimarães et al. "Screening of Filamentous Fungi for Production of Enzymes of Biotechnological Interest" (2006) Brazilian Journal of Microbiology, vol. 37: 474-480.*
Bakker, E., "Electrochemical Sensors" *Analytical Chemistry*, vol. 78, (2006) pp. 3965-3983.
Conyers, S.M., et al., "Chromogenic Substrates for Horseradish Peroxidase", *Analytical Biochemistry*, vol. 192, (1991) pp. 207-211.
Davidsson, R., et al., "Microfluidic biosensing systems part I. Development and optimization of enzymatic chemiluminescent μ-biosensors based on silicon microchips" *Lab on a Chip-Minaturisation for Chemistry and Biology*, vol. 4 (2004) pp. 481-487.
Kiss, T., "Purification and characterization of an extracellular β-D-xylosidase from *Aspergillus carbonarius*", http://cat.inist.fr/?aModele=afficheN&cpsidt=1532452, retrieved on Oct. 13, 2009.
Luong, J.H.T., et al., "Monintoring the activity of glucose oxidase during the cultivation of *Aspergillus niger* using novel amperometric sensor with 1,1'-dimethyferricinium as a mediator", *Biosensors and bioelectronics*, vol. 9, No. 8, (1994) pp. 577-584.
Perrone, G., et al., "Ochratoxin A Production and Amplified Fragment Length Polymorphism Analysis of *Aspergillus carbonarius, Aspergillus tubingensis*, and *Aspergillus niger* Strains Isolted from Grapes in Italy", *Appl. Environ. Microbiology*, vol. 72, No. 1, pp. 680-685 (2006).
Pollastro, S., et al., "A New Semi-Selective Medium for the Ochratoxigenic Fungus *Aspergillus carbonarius*", Journal of Plant Pathology (2006) vol. 88, No. 1, pp. 107-112.

(Continued)

*Primary Examiner* — Jon P Weber
*Assistant Examiner* — Teresa E Knight (57) ABSTRACT

Methods and kits are disclosed for detecting microorganisms that produce glucose oxidase. The method includes providing a culture medium and a hydrogen peroxide indicating reagent comprising a chromogenic substrate that can provide a detectable chromogenic reaction indicating the presence of a microorganism that produces glucose oxidase, and additional methods are disclosed for differentiating microorganisms by the detection of an additional chromogenic reaction.

12 Claims, 3 Drawing Sheets

(56) References Cited

OTHER PUBLICATIONS

Puchart, et al., "A simple enzymatic synthesis of 4-nitrophenyl β-1, 4-D-xylobioside, a chromogenic substrate for assay and differentiation of endoxylanases", *Journal of Biotechnology*, vol. 128 (2007), pp. 576-586.

Wong, et al., "Glucose oxidase: natural occurrence, function, properties and industrial applications", Appl. Microbiol. Biotechnol vol. 78 (2008), pp. 927-938.

* cited by examiner

RAPID DETECTION OF MOLDS THAT PRODUCE GLUCOSE OXIDASE

CROSS REFERENCE TO RELATED APPLICATIONS

This application is a national stage filing under 35 U.S.C. 371 of PCT/US2010/61552, filed Dec. 21, 2010, which claims priority to U.S. Provisional Patent Application No. 61/291,144, filed Dec. 30, 2009, the disclosures of which are incorporated by reference in their entirety herein.

FIELD

The present disclosure relates to methods of detecting microorganisms that produce glucose oxidase and kits for detecting microorganisms that produce glucose oxidase.

BACKGROUND

In various industries, such as the dairy, fruit juice, wine, and beer industries, there is a need to assay bacteria and molds. The art does not always distinguish mold assays from bacterial assays when devices for the assay of microorganisms are discussed, but it is known to those skilled in the art that mold assays are often slower than bacterial assays. Methods for detecting low concentrations of mold species typically rely on growth media, such as 3M PETRIFILM™ Yeast and Mold Count Plates or acidified potato dextrose agar. Agar treated with antibiotics, such as chloramphenicol, is also used. These methods take 3 to 7 days to produce a definitive answer, depending on the growth rate of the organism. Food manufacturers in particular desire a faster-responding test, since other growth related test results such as total aerobic (viable) count for bacteria are available within two days, and waiting an extra day or more to get yeast and mold test results is costly. Fluorescence microscopy or flow cytometry may provide a more immediate test result, but these technologies are prohibitively expensive.

The mold species *Aspergillus niger* is a common fungal food contaminant. Although generally non-pathogenic, it does cause black rot or smut disease on various fruits and vegetables. *A. niger* is also commonly found in indoor environments, where the colonies can be mistaken for the toxin-producing *Stachybotrys* mold.

In the viticulture industry, there is a need for improved discrimination between *Aspergillus niger* and *Aspergillus carbonarius*. The latter is the primary source in grapes of Ochratoxin A, a mycotoxin that is nephrotoxic, teratogenic, carcinongenic and suppresses the immune system. *A. niger* and *A. carbonarius* are difficult to distinguish by eye and are primarily differentiated on the basis of morphology by experienced mycologists using microscopy. Technologies exist to detect Ochratoxin A directly, based on liquid chromatography or immunoassays, but these methods are also costly and require expertise.

Other techniques for the detection of fungi that produce ochratoxin have been pursued. For example, U.S. Pat. No. 7,560,234 (Dobson et al.) putatively describes polymerase chain reaction (PCR) assay techniques that may be used in the detection and/or identification of an ochratoxinogenic fungus.

There is a need for methods that enable rapid detection and discrimination of *A. niger* and *A. carbonarius* and related species in a simple, cost effective manner.

SUMMARY

The present disclosure includes simple articles and methods to detect and/or identify microorganisms that produce glucose oxidase, including certain species of *Aspergillus* molds. In some embodiments, the inventive methods provide for the differentiation of certain *Aspergillus* species. Additionally, or alternatively, some embodiments provide for the enumeration of microorganisms that produce glucose oxidase. In some embodiments, the inventive methods provide for the automated detection and/or enumeration of microorganisms that produce glucose oxidase.

In one aspect, the present disclosure provides a method of detecting a microorganism that produces glucose oxidase. The method can comprise providing a thin film culture device comprising a cold-water-soluble gelling agent, a culture medium to support the growth of a microorganism that produces glucose oxidase, a hydrogen peroxide indicating reagent comprising horseradish peroxidase and at least one chromogenic substrate, and a sample suspected of containing the microorganism. The method further can comprise combining, in the culture device, a predetermined volume of the sample, the culture medium, and the hydrogen peroxide indicating reagent. The method further can comprise incubating the culture device, and then detecting a reaction of the chromogenic substrate. In some embodiments, the reaction of the chromogenic substrate is detectable within 48 hours of the start of incubating the culture device. In some embodiments, the culture device comprises the culture medium.

In another aspect, the present disclosure provides a method of detecting microorganisms that produce glucose oxidase. The method can comprise providing a thin film culture device comprising a cold-water-soluble gelling agent, a culture medium to support the growth of a microorganism that produces glucose oxidase, a hydrogen peroxide indicating reagent comprising horseradish peroxidase and at least one chromogenic substrate, and a sample suspected of containing the microorganism. The method further can comprise combining a predetermined volume of sample and the culture medium to form a first mixture, and then combining, in the culture device, the first mixture and the hydrogen peroxide indicating reagent. The method further can comprise incubating the culture device and then detecting a reaction of the chromogenic substrate. In some embodiments, the reaction of the chromogenic substrate is detectable within 48 hours of the start of incubating the culture device.

In any of the above embodiments, incubating the culture device can comprise incubating the device aerobically. In any of the above embodiments, the reaction of the chromogenic substrate may be detectable within 24 hours of the start of incubating the culture device. In any of the above embodiments, the microorganism can be selected from the group consisting of, for example, *Aspergillus niger*, *Aspergillus carbonarius*, *Aspergillus brasiliensis*, *Aspergillus tubingensis*, *Penicillium amagasakiense*, and *Penicillium funiculosum*.

In any of the above embodiments, the chromogenic substrate can be selected from the group consisting of, for example, 4-aminoantipyrine (4-AAP), 5-bromo-4-chloro-3-indolyl phosphate (BCIP), or a combination thereof. In some embodiments, the chromogenic substrate can further comprise 3-(N-ethyl-3-methylanilino)-2-hydroxypropanesulfonic acid sodium salt (TOOS).

In some embodiments, the method can further comprise differentiating the microorganism by detecting a reaction with a chromogenic β-D-xylopyranosidase substrate. In some embodiments, the chromogenic β-D-xylopyranosidase substrate can be selected from the group consisting of, for example, o-nitrophenyl-β-D-xylopyranoside and p-nitrophenyl-β-D-xylopyranoside (NXP).

In another aspect, the current disclosure provides a kit. The kit can comprise a thin film culture device comprising a cold water-soluble gelling agent, a culture medium to support the growth of a microorganism that produces glucose oxidase, and a hydrogen peroxide indicating reagent comprising horseradish peroxidase and at least one chromogenic substrate. In some embodiments, the chromogenic substrate can be selected from the group consisting of, for example, 4-aminoantipyrine (4-AAP), 5-bromo-4-chloro-3-indolyl phosphate (BCIP), or a combination thereof. In some embodiments of the kit, the kit can further comprise 3-(N-ethyl-3-methylanilino)-2-hydroxypropanesulfonic acid sodium salt (TOOS).

In some embodiments of the kit, the kit can further comprise a chromogenic β-D-xylopyranosidase substrate for the detection of microorganisms that produce β-D-xylopyranosidase. The chromogenic β-D-xylopyranosidase substrate may be selected from, for example, the group consisting of o-nitrophenyl-β-D-xylopyranoside and p-nitrophenyl-β-D-xylopyranoside (NXP).

In any one of the above embodiments of the kit, the culture medium can comprise the hydrogen peroxide indicating reagent. In some embodiments of the kit, the culture device can comprise the culture medium, the hydrogen peroxide indicating reagent, or both. In any one of the above embodiments of the kit, the kit can further comprising a sample preparation accessory selected from the group consisting of, for example, a sample diluent, a buffer, a sample acquisition device, and a pipette.

These and other aspects of the invention will be apparent from the detailed description below. The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. In no event should the above summaries be construed as limitations on the claimed subject matter, which subject matter is defined solely by the attached claims, as may be amended during prosecution.

DETAILED DESCRIPTION

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways. Also, it is to be understood that the phraseology and terminology used herein is for the purpose of description and should not be regarded as limiting. The use of "including," "comprising," "containing," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure is generally directed to methods and articles for detecting and differentiating *Aspergillus niger* and/or *Aspergillus carbonarius* microorganisms and related species in a sample. The inventive methods provide for growth, detection and differentiation of these microorganisms by detecting the presence of certain enzymes produced in levels that are detectable within 24 to 48 hours or less when the chromogenic substrates of the invention are employed. While not being bound by any particular theory, it is thought that species of microorganisms that produce glucose oxidase will, in the presence of a suitable substrate and reaction conditions, generate hydrogen peroxide, which may in turn be detected. The current disclosure provides a hydrogen peroxide indicating reagent that enables detection of glucose oxidase-producing microorganisms within 48 hours of incubation in a culture device, or within 42 hours of incubation in a culture device, or within 26 hours of incubation in a culture device, or even within 24 hours of incubation in a culture device.

Hydrogen Peroxide Indicating Reagent

The hydrogen peroxide indicating reagent of the current description includes a peroxidase enzyme and a chromogenic substrate. Preferably, the peroxidase enzyme is horseradish peroxidase. The reaction of horseradish peroxidase and hydrogen peroxide in the presence of at least one chromogenic substrate is known in the art to produce a reaction of the chromogenic substrate. However, it is believed that the selection of at least one chromogenic substrate to enable detection of a glucose oxidase-producing microorganism within 48 hours, or within 42 hours, or within 26 hours, or even within 24 hours of incubation in a culture device by means of a hydrogen peroxide indicating reagent has not been described previously.

Examples of a chromogenic substrate of the current description include 5-bromo-4-chloro-3-indolyl-phosphate (BCIP, Sigma Aldrich Chemical Co., Milwaukee, Wis.). In some exemplary cases of this description, the culture device is a commercially available thin film device (e.g., 3M PETRIFILM™ Yeast and Mold Count Plate) that includes BCIP as a phosphatase detection agent. It is found herein that by adding horseradish peroxidase and additional BCIP, an earlier detection of glucose oxidase-producing organisms may be obtained.

BCIP

Another example of a chromogenic substrate of the current description is 4-aminoantipyrene (4-AAP, Sigma Aldrich Chemical Co., Milwaukee, Wis.), which may also be used in combination with additional BCIP. It was also observed herein that the additional combination of 3-(N-ethyl-3-methylanilino)-2-hydroxypropanesulfonic acid sodium salt (TOOS, Sigma Aldrich Chemical Co., Milwaukee, Wis.) with 4-AAP, or with 4-AAP in combination with additional BCIP, provided enhancement of detectable chromogenic reaction over examples having only 4-AAP as the added chromogenic substrate.

TOOS

4-AAP

Suitable concentration levels of the components of the hydrogen peroxide indicator reagent may be selected to accommodate the particular embodiments of the description. Concentration levels of horseradish peroxidase that enable the currently described detection include 0.5 µg/mL to 50 µg/mL, including the exemplary level of about 10 µg/mL. Concentrations of 4-AAP and TOOS that enable the currently described detection include 0.1 mg/mL to 5 mg/mL, including the exemplary range of from about 0.5 mg/mL to about 1.0 mg/mL.

Chromogenic β-D-Xylopyranosidase Substrates

In order to provide for differentiation of glucose oxidase-producing microorganisms, a different chromogenic substrate may be included that is capable of reacting with a different enzyme produced by the microorganisms, thereby providing a differentiable reading among a subset of the microorganisms of interest. For example, in the case of *A. carbonarius* and several other microorganisms, the enzyme β-D-xylopyranosidase may be produced during incubation, while other microorganisms in a sample may produce little or no β-D-xylopyranosidase. A chromogenic xylopyranosidase substrate capable of reacting with β-D-xylopyranosidase may therefore produce a detection via chromogenic reaction different from the detection obtained with the use of the hydrogen peroxide indicating reagent alone. An example of a suitable chromogenic β-D-xylopyranosidase substrate is p-nitrophenyl-β-D-xylopyranoside (NXP, Sigma Aldrich Chemical Co., Milwaukee, Wis.):

NXP

Other suitable synthetic substrates for β-D-xylopyranosidase may be employed including o-nitrophenyl-β-D-xylopyranoside, or fluorophores such as 4-methylumbelliferyl-β-D-xylopyranoside or 6-bromo-2-naphthyl-β-D-xylopyranoside. Other chromogenic, fluorogenic or luminescent substrates of β-D-xylopyranosidase may be used, including synthetic substrates based on indolyl- and fluorescein-β-D-xylpyranoside analogs which would generate color, fluorescence, or luminescence by the elimination of a xylopyranoside moiety.

Chromogenic, fluorogenic or luminescent substrates of enzymes other than β-D-xylopyranosidase could similarly aid in the differentiation of glucose oxidase producing organisms, where a given enzyme (e.g., a phosphatase, glycosidase, peptidase, nuclease, or lipase) is produced by one glucose oxidase producing organism, and the same enzyme is not produced (or produced in much lower amounts) by another glucose oxidase producing organism.

Samples

Suitable samples can be obtained or derived from a variety of sources. The term "source" is generally used to refer to the food or nonfood desired to be tested for microorganisms. The source can be a solid, a liquid, a semi-solid, a gelatinous material, gas (e.g., air), and combinations thereof. In some embodiments, the source can be provided by a capture element that was used, for example, to collect the source from a surface of interest or from air. In some embodiments, the liquid composition can include the capture element, which can be further broken apart (e.g., during an agitation or dissolution process) to enhance retrieval of the source and any microorganism of interest. The surface of interest can include at least a portion of a variety of surfaces, including, but not limited to, walls (including doors), floors, ceilings, drains, refrigeration systems, ducts (e.g., air ducts), vents, toilet seats, handles, doorknobs, handrails, countertops, tabletops, eating surfaces (e.g., trays, dishes, etc.), working surfaces, equipment surfaces, clothing, etc., and combinations thereof. All or a portion of the source can be used in the method. When a portion of the source is used, this can sometimes be referred to as a "sample" of the source. However, the term "sample" is generally used herein to refer to the portion of volume or mass of material that is obtained from the source and is introduced into a test device for the detection of microorganisms.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages (including juices, beers and wines), water, animal feed, other suitable comestible materials, and combinations thereof.

Samples such as food (e.g., grapes) may be processed by various means to enhance the release of microorganism for analysis. The sample is subjected to a strenuous mixing process, such as blending or stomaching, to create a relatively homogeneous liquid suspension. The samples are frequently processed in a plastic sample reservoir which is called a stomacher bag.

In some embodiments, the source of the sample may include water from industrial processing ("process water"), or environmental water.

"Sample acquisition device" is used herein in the broadest sense and refers to an implement used to collect a liquid, semisolid, or solid sample material. Non-limiting examples of sample acquisition devices include swabs, wipes, sponges, scoops, spatulas, tongue depressors, filters, pipettes, pipette tips, and siphon hoses.

Various sampling techniques for the detection of microbes on surfaces are known. Such sampling techniques are suitable for the methods of the present invention as well. For example, it is common to obtain a sample from wiping the surface of food processing equipment or from wiping the nares of a patient. A particularly preferred sampling technique includes contacting (e.g., swabbing, wiping) the surface with a sterile swab, sponge, or sampling device.

A wide variety of swabs or other sample collection devices are commercially available, for example, from 3M Company, St. Paul, Minn., under the trade designation 3M™ Quick Swab, from Puritan Medical Products Co. LLC, Guilford, Me., under the trade designation PURE-WRAPS or from Copan Diagnostics, Inc. Corona, Calif., under the trade designation ESWAB, or from microRheologics, S.r.l., Brescia, TT, under the trade designation FLOCKEDSWAB. A sample collection means such as that disclosed, for example, in U.S. Pat. No. 5,879,635 (Nason) can also be used if desired. Swabs can be of a variety of materials including cotton, rayon, calcium alginate, Dacron, polyester, nylon, polyurethane, and the like.

The sample collection device (e.g., swab) can then be cultured directly, analyzed directly, or extracted (e.g., by washing, elution by vortexing) with an appropriate solution.

Such extraction (i.e., elution) solutions typically include water and can optionally include a buffer and at least one surfactant. An example of an elution buffer includes, for example, phosphate buffered saline (PBS), which can be used in combination, for example, with TWEEN 20 or PLURONIC L64. The test sample (e.g., liquid) may be subjected to treatment prior to further analysis. This includes concentration, precipitation, filtration, centrifugation, dialysis, dilution, inactivation of natural components, addition of reagents, chemical treatment, etc.

Culture Devices

Environmental factors that may affect the growth of *Aspergillus* microorganisms can include the presence or absence of nutrients, pH, moisture content, salt content, oxidation-reduction potential, antimicrobial compounds, temperature, atmospheric gas composition and biological structures or barriers.

Nutrient media for culturing *Aspergillus* species are known in the art. A commonly employed medium for growing fungi is potato dextrose agar, which may, for example, include potato starch (4 g/L), dextrose (20 g/L), and agar (15 g/L). Another general medium for fungal growth is malt extract agar which may be prepared as a mixture of maltose (12.75 g/L), dextrin (2.75 g/L), glycerol (2.35 g/L), peptone (0.78 g/L) and agar (15 g/L). These growth media are available from Beckton Dickinson (Franklin Lakes, N.J.).

The present disclosure in certain embodiments includes culture devices for the detection of *Aspergillus* molds. Culture devices of the present invention include, for example, thin film culture plate devices. Thin film culture plate devices are typically more compact than traditional agar Petri dishes and typically contain dry, rehydratable culture medium to support the growth of certain microorganisms. Non-limiting examples of thin film culture plate devices include the coated-substrate devices disclosed in U.S. Pat. Nos. 4,565,783; 5,089,413, and 5,681,712; each of which is incorporated herein by reference in its entirety.

Figure 1:
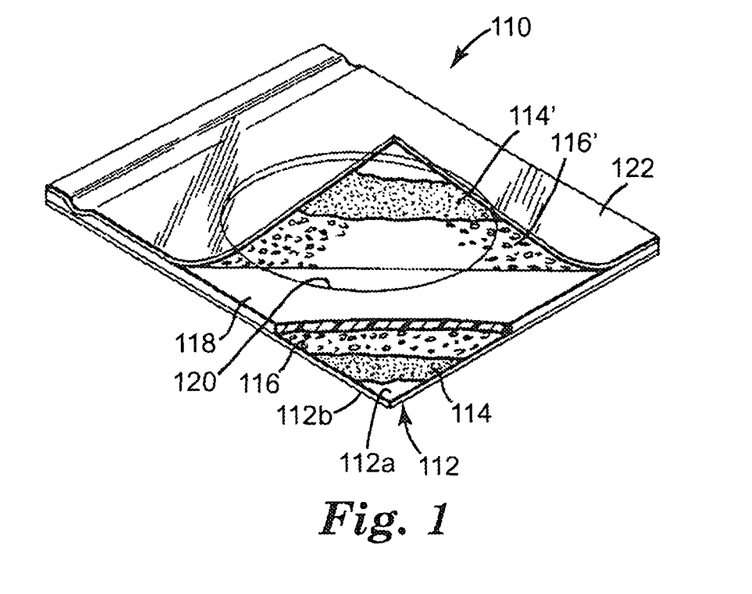
FIG. 1 is a top perspective view, partially in section, of an embodiment of a thin film culture device.
Figure 2:
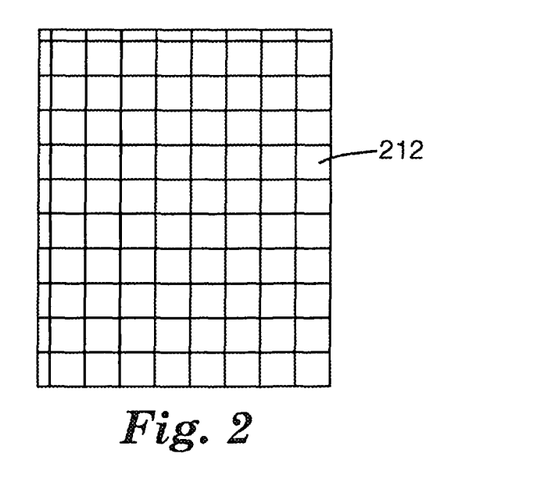
FIG. 2 is a top view of one embodiment of a self-supporting substrate comprising a grid pattern.

FIG. 1 illustrates an embodiment of a thin film culture device in accordance with the present invention. The culture device 110 includes a body member comprising a self-supporting water-proof substrate 112 having upper and lower surfaces (112a and 112b, respectively). Substrate 112 can be a relatively stiff film (e.g., polyester, polypropylene or polystyrene), which will not absorb or otherwise be affected by water. The substrate 112 may be either transparent or opaque, depending on whether one wishes to view microbial colonies through the substrate. To facilitate the counting of mold colonies, the substrate 212 can have a grid pattern (e.g., squares) printed thereon, as shown in FIG. 2.

Referring to FIG. 1, substrate 112 can be coated on its upper surface 112a with a layer of an adhesive 114 which serves to hold the dry gelling agent, chromogenic indicator, and/or nutrients in a uniform monolayer for easy hydration. Adhesive 114 should be coated onto substrate 112 in a thickness which is preferably less than the diameter of the particles of the powdered gelling agent and/or nutrients. The object is to apply enough adhesive to adhere the particles to the substrate but not so much that the particles become completely embedded in the adhesive. A uniform monolayer of cold-water-soluble powder 116 is desired with sufficient surface area exposed for hydration. Also shown in FIG. 1 are optional adhesive 114' and cold-water-soluble powder 116' layers on cover sheet 122. When hydrated with an aqueous solution (e.g., the sample and/or an aqueous suspending medium, such as water or a buffer), the gelling agent forms a hydrogel.

In some embodiments, adhesive 114 can comprise a water-based adhesive composition. Preferably, the layer of water-based adhesive 114 is sufficiently transparent when wetted by an aqueous test sample to enable the viewing of the colonies of microorganisms. The water-based adhesive composition can incorporate one or more hydrophilic agents, including nutrients, selective agents, indicators (e.g., chromogenic indicators), or combinations thereof.

The dry culture medium can optionally include reagents necessary for carrying out certain microbiological tests. To grow a yeast or mold sample without interference from bacteria, certain bacteriostatic agents such as chloramphenicol, chlortetracycline, tartaric acid, or a suitable penicillin may be included in the dry medium.

An exemplary useful class of indicators include dyes that are metabolized by, or otherwise react with, growing microorganisms, and in so doing cause the microbial colonies to be colored or fluoresce for ease of detection and/or quantitation by a technician or by an automated reader. Non-limiting examples of such dyes include triphenyltetrazolium chloride, p-tolyltetrazolium red, tetrazolium violet, veratryl and tetrazolium blue. However, it will be appreciated that other suitable dyes can be used depending on the particular organism(s) to be identified. It will be appreciated by a person of ordinary skill in the art that any other indicator, dye, selective agent, enzyme substrate, or nutrient used in accordance with the present invention should not substantially interfere with the observation and/or imaging of the glucose oxidase indicator described herein.

A buffering reagent, such as sodium carbonate, can be employed to provide a medium exhibiting a neutral pH and "Cab-O-Sil M-5" can be employed as a processing aid, as described in U.S. Pat. No. 4,565,783, which is incorporated herein by reference in its entirety. Of course, the particular coating mixture (e.g., nutrients, indicators, and/or gelling agents) used for powder 116 may be adjusted depending upon the type of microorganisms to be grown.

It is also contemplated within the scope of the invention that powder 116 may optionally include additional reagents necessary for carrying out certain biochemical tests for microorganism identification. Such reagents (e.g. an enzyme substrate), which undergo a color change in the presence of a particular type of microorganism, may be included in the powder 116 or adhesive 114.

In another embodiment of the invention, powder 116 may comprise a coating that includes a mixture of a gelling agent and a nutrient, a selective agent, and/or an indicator which has been dissolved or suspended in a solution, coated and dried onto substrate 112. In this embodiment, the coating is substantially water-free (i.e., the coating has a water content no greater than about the water content of the dehydrated coating once it has been permitted to equilibrate with the ambient environment).

As depicted in FIG. 1, the body member can include a spacer 118 applied to the upper surface of substrate 112, the spacer 118 comprising a circular aperture 120 cut through the center to expose the powder 116 on substrate 112. The walls of aperture 120 provide a well of predetermined size and shape to confine the medium following hydration. The aperture 120 generally delineates the growth area of the culture device 110. Spacer 118 should be thick enough to form a well of the desired volume, e.g., 1, 2 or 3 milliliters. Closed cell polyethylene foam is a preferred material for spacer 118, but any material which is hydrophobic (non-wetting), inert to microorganisms, and capable of withstanding sterilization may be used. In some embodiments (not shown), the spacer 118 can comprise a plurality of apertures 20 (e.g., 2, 3, 4, 5, 6, 7, 8, 9, 10, 12, 15, or 20 apertures), each of which can be inoculated with a distinct liquid sample.

Spacer 118 can include relatively thick designs, such as those described in U.S. Pat. No. 5,681,712, which is incorporated herein by reference in its entirety. One purpose of the thicker apertured spacer 118 is to locate and protect membranes (e.g. microporous filter membranes) placed in the aperture 120 of the spacer 118 (not shown). Another purpose of the thicker spacer 118 is to reduce or prevent contact by cover sheet 122 with the growing colonies of microorganisms (i.e., provide a "head space" between the growth surface and the cover sheet 122, which can also provide increased aeration for growing colonies of microorganisms).

The thickness of spacer 118 should be sufficient to enclose the liquid volume added to the culture device when the device is inoculated. Depending upon the thickness of the membrane, when used, the spacer can be at least about 0.5 mm thick, about 1 mm thick, about 1.5 mm thick and about 2 mm thick.

Figure 3:
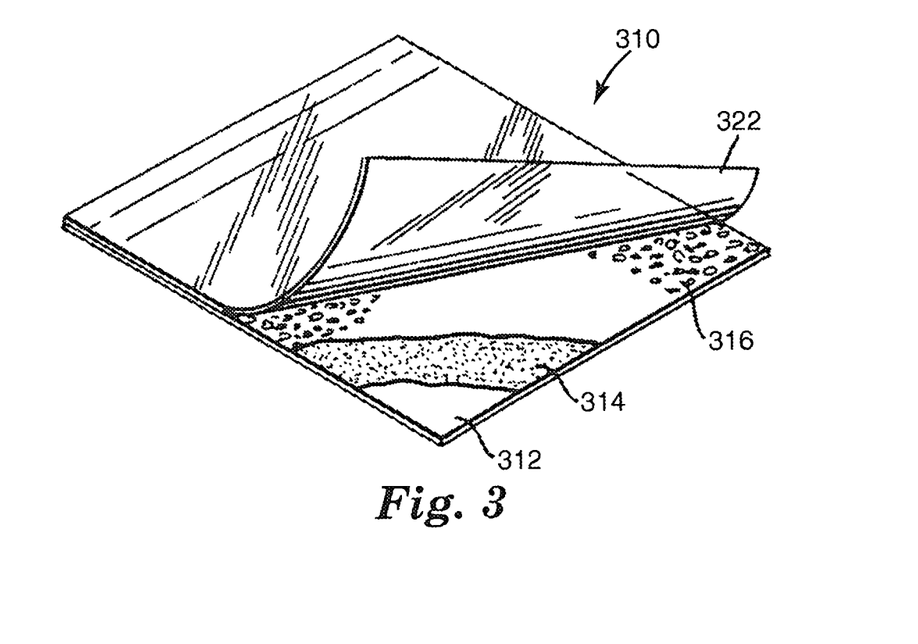
FIG. 3 is a top perspective view, partially in section, of an embodiment of a thin film culture device.

FIG. 3 shows another embodiment of a thin film culture device 310. This embodiment includes substrate 312, adhesive 314, cold-water-soluble powder 316, and cover sheet 322, as described in FIG. 1.

In contrast to the culture device 110 of FIG. 1, the device 310 of FIG. 3 does not include a spacer to confine the sample during inoculation. A template, e.g., a weighted ring (not shown), may be applied temporarily to the outside of cover sheet 322, after closing, to confine the sample to a specific region while the cold-water-soluble powder 316 forms a gel. The portion of the culture device 310 inoculated with a sample generally delineates a growth area of the device 310. In some embodiments, the device 310 can be inoculated with a plurality (e.g., 2, 3, 4, 5, 6, 7, 8, 9, 10, 12, 15, or 20) of distinct liquid samples, using appropriate spacing and templates to confine the separate samples to distinct portions of the powder 316 of the culture device 310. When hydrated with an aqueous solution (e.g., the sample and/or an aqueous suspending medium, such as water or a buffer), the cold-water soluble powder comprising a gelling agent forms a hydrogel.

Figure 4:
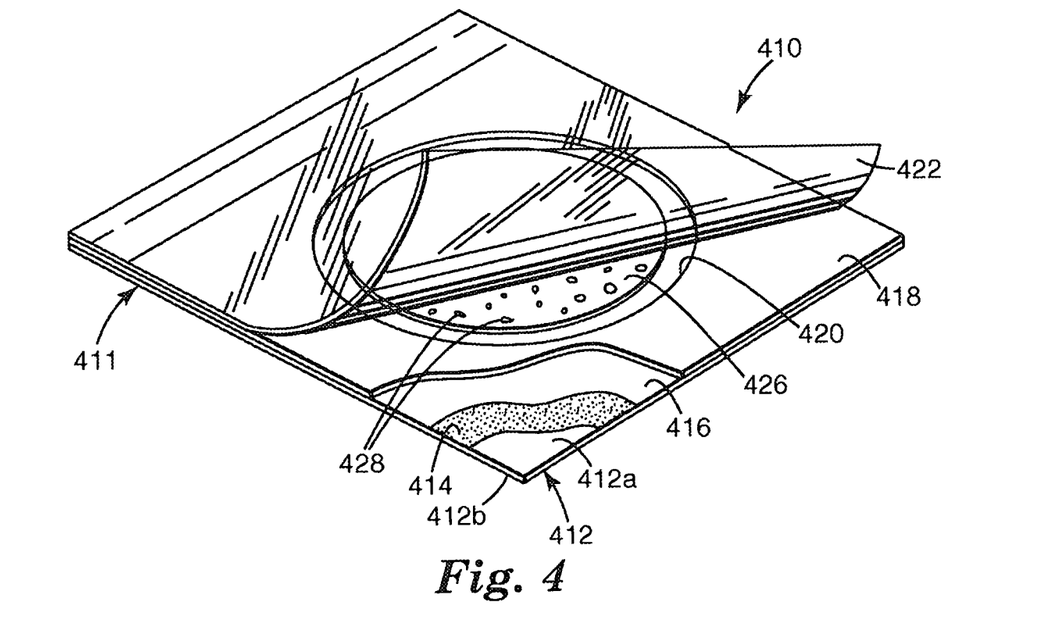
FIG. 4 is a top perspective view, partially in section, of an embodiment of a thin film culture device comprising a spacer and a capture element.

In one embodiment, a thin film culture plate device can be made by producing a liquid coating mixture, coating the liquid coating mixture onto a substrate, drying the coated substrate and, optionally, attaching a cover sheet according to processes described in U.S. Pat. No. 4,565,783, which is incorporated herein by reference in its entirety, for example. An exemplary device of this embodiment is shown in FIG. 4. The thin film culture device 410 includes a body member 411 having a self-supporting, waterproof substrate 412 having upper and lower surfaces 412a and 412b, respectively. Substrate 412 is preferably a relatively stiff material made of a waterproof material that does not absorb water such as polyester, polypropylene, or polystyrene. Other suitable waterproof materials include substrates such as paper containing a waterproof polyethylene coating. The upper surface 412a is coated with a liquid composition, which is then dried to provide a dry coating 416 on substrate 412. The dry coating 416 comprises a cold-water soluble gelling agent as described herein and may also include a nutrient, a selective agent, an indicator, a pH indicator, or a combination of any two or more of the foregoing. The liquid composition used to produce the dry coating 416 may be readily dried by heating liquid composition in an oven at about 104° C. until essentially all of the water in the composition has evaporated. If the composition is heated after the water has evaporated, however, certain components of the composition (e.g., nutrients, indicators) may begin to degrade. In use, the dry coating 416 is hydrated with a liquid (e.g., a liquid sample and/or a liquid nutrient medium) to form a reconstituted liquid composition.

A layer of adhesive 414 may be coated on substrate 412. The adhesive may serve to hold the dry coating 416 to the substrate 412. The adhesive should be sufficiently transparent when hydrated to allow viewing of colonies growing on the surface of the coated substrate 412. The adhesive should also be coated on the substrate 412 in a thickness which allows the substrate to be uniformly coated with dry coating 416 without completely embedding the coating in the adhesive.

A spacer 418 having a generally circular aperture 420 is adhered to the dry coating 416 and/or the substrate 412. The spacer 418 covers the periphery of substrate 412 and the aperture 420 defines the area that is to be inoculated with a sample. Spacer 418 circumscribes the growth area of the device 410 and serves to prevent a liquid sample from leaking from the substrate 412. In an alternative embodiment, device 410 may not include a sample-containing spacer 418. In this device (not shown), the sample can be contained on the substrate during inoculation using the weighted circular template described above and is contained during incubation by the components (e.g., the gelling agent) of the medium alone.

A cover sheet 422 is attached to an edge of an upper surface of the foam spacer 418. Cover sheet 422 is preferably made of a transparent film or sheet material in order to facilitate counting of microorganism colonies present on the substrate. In addition, cover sheet 422 is preferably impermeable to bacteria and water vapor in order to avoid the risk of contamination and deterioration of the components. A preferred material for use as a cover sheet 422 is biaxially-oriented polypropylene. Optionally, the coversheet 422 may be coated with a layer of adhesive, which may be coated with a dried composition (e.g., powders) comprising a gelling agent, nutrients, selective agents, an indicator (e.g., a pH indicator), or a combination of any two or more of the foregoing (not shown).

In use, a predetermined amount of inoculum, typically about one milliliter of a liquid inoculum is added to the device illustrated in FIG. 4 by pulling back the cover sheet and distributing the inoculum onto the dry coating 416. The inoculum may optionally comprise a nutrient, a selective agent, an indicator or a combination of any two or more of the foregoing. Cover sheet 422 is then replaced over the coating 417 and the inoculum is evenly spread inside the circular opening of the foam spacer 418. A convenient tool to do this is a weighted circular template. As the inoculum contacts and is spread on coating 417, the coating hydrates to form a gel. Nutrients present in the gel can support the growth of microorganisms. The inoculated device is then incubated for a predetermined time after which the number of colonies growing on the substrate may be observed through the transparent cover sheet 422 and counted.

A capture element, such as a membrane filter, can optionally be used with device 410. FIG. 4 shows a membrane filter 426 positioned in the aperture 420 of the spacer 418. Also shown are microorganism colonies 428 growing on the membrane filter 426. Suitable microporous membranes do not substantially interfere with the production of glucose oxidase and/or β-D-xylopyranosidase, or other enzymes of interest by the microorganisms of this description or with the detection of the microorganisms using the hydrogen peroxide indicating reagent. In certain preferred embodiments, the microporous membranes are substantially transparent when contacted with the reconstituted liquid composition. The membrane filter 426 can be positioned in the device 410 before liquid is added to the device 410 to reconstitute the dry coating 416. The membrane filter 426 can be positioned in the device 410 after liquid is added to the device 410 to reconstitute the dry coating 416. In some embodiments, the membrane filter 426 may comprise enough liquid to reconstitute the dry coating 416 when the filter 426 is positioned in the device 410.

The culture medium of the present invention may include nutrients, salts and ions generally suitable to promote the growth of target (i.e., glucose oxidase-producing and/or β-D-xylopyranosidase-producing) microorganisms when the culture medium is inoculated with a sample suspected of containing the target microorganisms. Culture media containing components such as, for example, nutrients, salts, ions, selective agents, indicators, and the like can be tested with known *Aspergillus* species to determine that the components promote the growth of the target microorganism, inhibit the growth of non-target microorganisms, and/or do not interfere with the production of glucose oxidase and/or β-D-xylopyranosidase by the microorganisms or with the detection of glucose oxidase and/or β-D-xylopyranosidase using the chromogenic substrate. The culture medium also may include one or more gelling agents. The culture medium of the present disclosure can include at least one selective agent that selects for growth of the mold species of interest.

Optionally, the culture medium can comprise a buffer. Suitable buffers include carbonate buffers, phosphate buffers, and sulfonate buffers. In some embodiments, the phosphate buffer is a potassium phosphate buffer. In some embodiments, the culture medium can comprise more than one buffering agent (e.g., potassium phosphate and sodium acetate). The phosphate buffer can be about 22 mM. In other embodiments, the buffer is a sulfonate species such as N-tris(hydroxymethyl)methyl-2-aminoethane sulfonic acid (TES) or the corresponding sodium salt; the TES buffer can be about 50 mM.

The concentration of each component in the culture medium is selected to provide a concentration suitable for growth and/or detection of the target microorganisms after the culture device has been inoculated. Suitable concentrations of nutrients and selective agents for growing the mold species of interest in culture media are known in the art. Suitable concentrations of the chromogenic substrates may be influenced by their intrinsic properties (e.g., solubility and their potential inhibitory properties toward certain target microorganisms).

The selection of target microorganisms may include inhibiting the growth of non-target microorganisms, promoting the growth of target microorganisms, or both. Promoting the growth of target microorganisms may be provided by the at least one first selective agent either directly (e.g., a nutrient that can be used by target microorganisms and not by other microorganisms), indirectly (e.g., by reducing competition for nutrients by inhibiting non-target microorganisms), or both directly and indirectly.

A dry culture medium according to the present invention may be applied to one or more surfaces of a thin film culture device in the following manner. The components of the culture medium may be dissolved in a solvent (e.g., water). The resulting solution may then be coated onto one or more surfaces of the device. The coating is then allowed to dry, leaving dried culture medium on the surfaces of the device that had been coated with the culture medium solution. The coating may be dried in any suitable manner including, but not limited to, air drying and heating.

The quantity of each component of the dry culture medium is at least partially determined by at least two factors: (1) the concentration of that component in the culture medium solution, and (2) the amount of the solution coated onto a given surface area of the culture device (the coating weight). Suitable coating weights may range from about 0.45 mg/cm$^2$ to about 2.5 mg/cm$^2$. In some embodiments, the culture medium nutrients may be coated separately from the indicators. In such embodiments, the coating weight for the culture medium nutrients may range from about 1.6 mg/cm$^2$ to about 2.5 mg/cm$^2$. In one embodiment, the coating weight of the nutrient coating is about 2.1 mg/cm$^2$. The coating weight for the indicator coating may range from about 0.45 mg/cm$^2$ to about 0.84 mg/cm$^2$. In one embodiment, the coating weight of the indicator coating is about 0.62 mg/cm$^2$.

Additional embodiments may include components of the hydrogen peroxide indicating system is Although the embodiments illustrated in FIGS. 1-4 have a cover sheet attached to the device, it is also contemplated within the scope of the invention that the powder-containing embodiments may be uncovered and simply placed in a sterile environment during storage and incubation.

Additional embodiments of culture devices are not excluded by the above description of thin film culture plate devices. For example, a method of detecting a microorganism that produces glucose oxidase may include inoculating a culture medium with a sample, wherein a hydrogen peroxide indicating reagent is present in the culture medium, the culture medium is incubated to produce a detectable chromogenic reaction, and wherein the culture medium is optionally agar contained in a traditional Petri dish.

Capture Element

Culture plate devices of the present disclosure can be used with a capture element to detect glucose oxidase-producing microorganisms present in a sample. As used herein, "capture element" refers to an article that is used to capture and retain microorganisms that are present in a sample. In some embodiments, the capture elements can be contacted transiently with the thin-film culture plate devices disclosed herein. For example, the sample may be captured on one side of a surface filter and that side of the filter can be contacted with growth area of the thin-film culture plate device, and thereby transfer sample material to the growth area, after the culture plate device has been hydrated. The surface filter can then be removed from the device prior to incubating the device. The capture element (e.g. a membrane filter) can be dimensioned to allow it to be placed into a thin film culture plate device of the present invention and, in certain preferred embodiments, the capture element remains in the thin film culture plate device during the incubation period for a sufficient period to allow for at least one cell division of the target microorganism. Placing the capture element into the culture plate device can bring the capture element in contact with a gelling agent and/or a culture medium, if present, in the culture plate device, allowing microorganisms to grow and/or proliferate. In some embodiments, the culture plate device is hydrated (e.g., inoculated with a sterile liquid or an unknown liquid sample) before the capture element is placed into the culture plate device. In some embodiments, the culture plate device is hydrated after the capture element is placed into the culture plate device.

Capture elements can be selected for their suitability with certain types of samples. For example, microporous membrane filters can be used as capture elements to retain microorganisms present in a liquid sample. The liquid sample can be passed through the filter and the microorganisms can be retained thereon. Microorganisms can be retained by, for example, physical entrapment or specific (e.g., antigen-antibody or receptor-ligand interaction) or nonspecific (hydrophobic adsorption) chemical interaction. Microporous membranes of the present disclosure, when present in the thin-film culture plate device, should permit the observation of a hemolytic reaction. Preferred microporous membrane filters become substantially transparent when wet.

Referring to the embodiment shown in FIG. 4, the test sample may comprise a liquid inoculum and/or a capture element 426 such as a microporous filter (e.g., a filter membrane) or a wipe device. Capture element 426 can be constructed from various membranes and/or films and can be used to capture microorganisms. In some embodiments, capture element 426 can provide a surface on which the colonies of microorganisms can be grown, detected and/or enumerated by the method and devices of the invention. Particularly suitable are known microporous filters which have been commonly used to separate small microorganism populations, such as molds from large fluid samples. Such filters are known to be placed on the surface of agar media and incubated to allow counting and evaluation of the filtered microbes. Suitable filters include the HAWG series, e.g., HAWG 047S6 type HA filter, available from Millipore Corp (Marlborough, Mass.). The microorganism filters described herein are generally relatively thin and may be provided in any desired 2-dimensional shape, e.g., as rectangles, as discs (including partial discs) and the like.

Microorganisms are separated by such filters with varying efficiency depending upon the sizes of the pores in the membranes. Microorganisms are typically captured by filters having a mean pore diameter of less than about 1 µm, less than about 0.8 µm, preferably, less than about 0.45 µm, more preferably, equal to or less than about 0.2 µm. Filtration is carried out by conventional methods using gravity or vacuum-assisted methods with funnels and discs of suitable sizes. Membrane filters are preferably handled aseptically with tweezers. Membrane filters may be made by the user from commercially available materials or are provided in aseptic packages as separate entities or as parts of kits of the invention.

Wipe devices can be used as capture elements with the culture plate devices of the present disclosure. As used herein, a "wipe device" is an article that is configured for contacting a surface to obtain a sample of microorganisms disposed thereon. Wipe devices can include porous, nonwoven materials. Non-limiting examples of wipe materials include paper (e.g., filter paper, cellulosic membrane filters), synthetic nonwovens (e.g., nylon or polyester nonwovens), polymeric or ceramic membranes (e.g., polycarbonate membranes, zirconia membranes), and microstructured films (e.g., microchannel-containing films such as those described in U.S. Pat. No. 7,223,364, which is incorporated herein by reference in its entirety). In some embodiments, the microchannel-containing films comprise through-holes that allow the passage of liquid (and solutes or small particles) from one major surface of the film to the other major surface. Wipe devices can include chemicals (e.g., surfactants), to improve wettability, or reagents (e.g., differential stains), provided the chemical or reagents do not adversely affect the detection of a reaction of the chromogenic substrate. Wipe devices in general comprise chemicals in an amount that will not substantially inhibit the growth of microorganisms under the inoculation and incubation conditions described herein. In some embodiments, the capture elements are substantially transparent or become substantially transparent when wet, allowing for the visualization of a differential reaction, such as hemolysis, through the capture element.

Suitable capture elements include a particle, or a plurality of particles. The capture elements can include a means for coupling the capture element to microorganisms. Non-limiting examples of particles include microspheres, microbeads, and the like. Such particles can be resin particles, for example, agarose, latex, polystyrene, nylon, polyacrylamide, cellulose, polysaccharide, or a combination thereof, or inorganic particles, for example, silica, aluminum oxide, or a combination thereof. Such particles can be magnetic, paramagnetic, superparamagnetic, or non-magnetic. Such particles can be colloidal in size, for example about 100 nm to about 10 microns (µm). Non-limiting examples of such particles include superparamagnetic polymer particles sold under the trade names DYNABEADS (Invitrogen, Inc., Carlsbad, Calif.) and BIO-ADEMBEADS (Ademtech, Pessac, France). Particle capture elements may be incorporated into other structures, such as a microporous membrane.

There are a variety of means for coupling capture element (e.g., a particle) to a microorganism. In some embodiments, the means for coupling the capture element to the microorganism can include surface molecules or properties that promote nonspecific adsorption. For example, at least a portion of the capture element can have molecules on its surface that, under the proper conditions (e.g., high pH or low pH), become positively- or negatively-charged and nonspecifically adsorb to complementary-charged molecules associated with the surface of a microorganism.

Additionally, or alternatively, at least a portion of the capture element (e.g., a polystyrene particle) can have a hydrophobic surface which nonspecifically adsorbs to hydrophobic molecules associated with the surface of a microorganism. In some embodiments, the means for coupling a capture element to a microorganism may comprise a molecule that specifically binds to a microorganism through a receptor-ligand interaction. Such specific receptor-ligand interactions are well known in the art and include interactions between, for example, antibodies and their corresponding antigens, lectins and their corresponding carbohydrate binding partner, bacteriophage proteins and their corresponding phage receptors, and the like. It should be understood that the means for coupling a particle to a microorganism can also be used in conjunction with film or non-woven (e.g., filter) capture elements, as well as the particulate capture elements.

Methods for Detecting Glucose Oxidase-Producing Microorganisms in a Sample

Detection of the glucose oxidase-producing microorganisms in the culture medium may be done visually or done by an instrument. Visual observation of a reaction of the chromogenic substrate is not limited to any particular lighting conditions, and may be done under ambient light conditions. The visual observation may optionally be further aided by the use of magnification.

Automated systems for counting microbial colonies in culture devices are known in the art. Such automated systems generally comprise an imaging system, an image analysis algorithm to determine a colony count, and a data management system to display and, optionally, store and manipulate the colony count data and images. An exemplary system for counting colonies on agar plates is sold by Synbiosis (Cambridge, UK) under the trade name PROTOCOL and in U.S. Pat. No. 6,002,789.

Systems for counting colonies on PETRIFILM plates are described in U.S. Pat. Nos. 5,403,722; 7,298,885; and 7,298,886, each of which is incorporated herein by reference.

Figure 5:
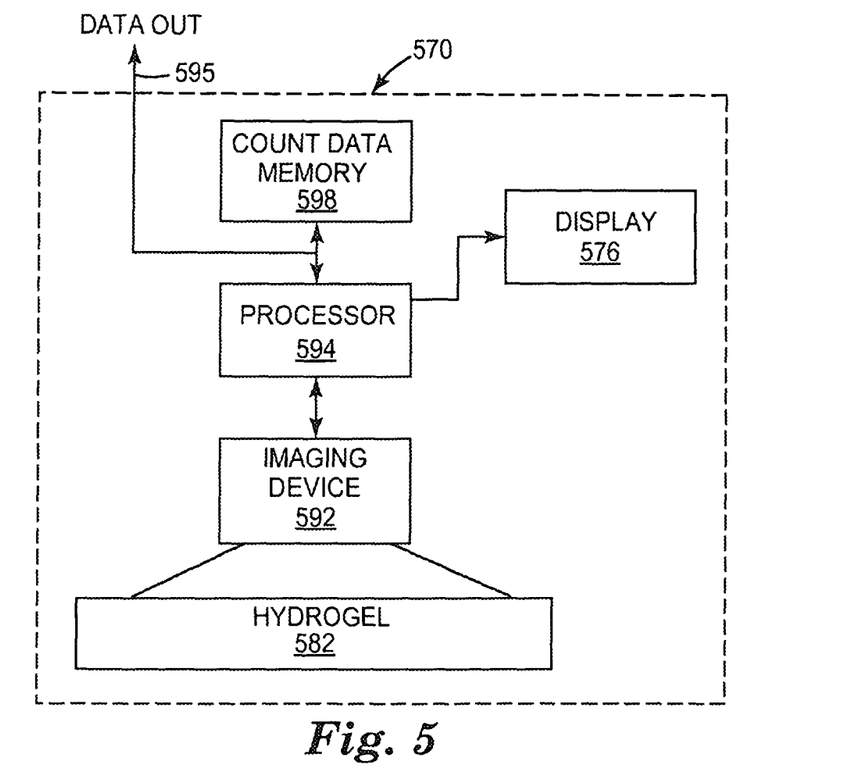
FIG. 5 is a block diagram of one embodiment of a detection system according to the present disclosure.

FIG. 5 is a block diagram illustrating internal operation of an imaging system 570. As illustrated in FIG. 5, a culture device 582 is positioned in a focal plane (e.g., on a platform, not shown) within an imaging system. In accordance with the invention, imaging device 592 may include multi-color illumination systems (not shown) for front and/or back illumination of culture device 582, as well as a monochromatic line or area scanner that captures an image of the culture device 582. In some embodiments, for example, imaging device 592 may take the form of a two-dimensional, monochromatic camera.

In general, imaging device 592 captures images of culture device 582, or at least a portion thereof, during illumination of the culture device with one or more different illumination colors. In some embodiments, multiple images of the same culture device 582 can be generated with various illumination durations or intensities and one or more of the multiple images can be selected for analysis. In some embodiments, selective illumination of a first side and a second side of the culture device 582 can be used to generate multiple images of the culture device and one or more of the images can be selected for analysis. Selection of an image for analysis can be based on, for example, the color contrast and/or object resolution properties of the individual images. Processes for determining the color contrast and object resolution properties of an image are known in the art and are disclosed in, for example, U.S. Pat. No. 6,243,286, which is incorporated herein by reference in its entirety.

A processor 594 controls the operation of imaging device 592. Also shown in FIG. 5 is optional display 576, which can receive an image from the processor 594 for visual review by an operator. In operation, processor 594 controls imaging device 592 to illuminate the culture device 582 and obtain an image. Processor 594 receives image data representing the scanned image from imaging device 592. In some embodiments, processor 594 can select an image, from multiple images, for analysis and/or display. Processor 594 analyzes at least one image of culture device 582 and may produce an analytical result, such as a count of colonies of glucose oxidase-producing organisms or a determination of the presence or absence of glucose oxidase-producing organisms s in a sample. The analytical result (e.g., a qualitative or quantitative result) can be displayed on display 576, stored in optional data storage memory 598, or retrieved by a host computer (not shown) via optional communication port 595.

Kits of the Invention

Kits provided by the present invention include a culture device comprising a cold water-soluble gelling agent, a culture medium to support the growth and identification of glucose oxidase-producing organisms, and a chromogenic indicator system. In some embodiments, the culture device can comprise the culture medium to support the growth and identification of glucose oxidase-producing organisms and/or the chromogenic indicator.

In some embodiments, the kit comprises a dehydrated culture medium to support the growth and identification of glucose oxidase-producing organisms. In some embodiments, the dehydrated culture medium comprises a chromogenic indicator.

In some embodiments, the kit comprises a liquid culture medium to support the growth and identification of glucose oxidase-producing organisms. In some embodiments, the liquid culture medium comprises a chromogenic indicator.

Kits of the present invention may further comprise a sample preparation accessory to assist in the preparation and/or inoculation of the sample. Non-limiting examples of sample preparation accessories include a diluent, a buffer, a sample acquisition device (e.g., a swab, a sponge, a spatula), and a pipette.

In further describing the embodiments of the invention, a first method is provided for detecting a microorganism that produces glucose oxidase, including the steps of:
  (a) inoculating a culture medium with a sample, wherein the culture medium includes a hydrogen peroxide indicating reagent comprising horseradish peroxidase and at least one chromogenic substrate, and wherein the sample is suspected of containing a microorganism that produces glucose oxidase;
  (b) incubating the culture medium under conditions that permit the growth of a microorganism that produces glucose oxidase; and
  (c) inspecting the culture medium to determine whether a microorganism that produces glucose oxidase is present.

A second method is provided that can have all of the features of the first method. In the second method, the culture medium can be a liquid medium, a semi-solid medium, a solid medium, or a reconstituted dry culture medium.

A third method is provided that can have all of the features of the first or second methods. In the third method, the step of incubating the culture medium under conditions that permit the growth of a microorganism that produces glucose oxidase comprises incubating the inoculated culture medium at a temperature of about 30° C.

A fourth method is provided that can have all of the features of the first through third methods. In the fourth method, the inoculated culture medium is incubated for about 24 hours.

A fifth method is provided that can have all of the features of the first through fourth methods. In the fifth method, the chromogenic substrate comprises a compound that produces a detectable signal in the presence of horseradish peroxidase and a growing microorganism that produces glucose oxidase.

A sixth method is provided that can have all of the features of the fifth method. In the sixth method, the detectable signal comprises a chemiluminescent signal, a fluorescent signal, a color change, a change in electrical conductivity, or any combination of any of the foregoing.

A seventh method is provided that can have all of the features of the fifth method. In the seventh method, the at least one chromogenic substrate comprises a compound selected from the group consisting of 5-bromo-4-chloro-3-indolyl phosphate (BCIP), 4-aminoantipyrine (4-AAP), and combinations thereof.

An eighth method is provided that can have all of the features of the seventh method. In the eighth method, the at least one chromogenic substrate further comprises 3-(N-ethyl-3-methylanilino)-2-hydroxypropanesulfonic acid sodium salt (TOOS).

A ninth method is provided that can have all of the features of the seventh or eighth methods. In the ninth method, inspecting the culture medium to determine whether a microorganism that produces glucose oxidase is present comprises detecting red colonies.

A tenth method is provided that can have all of the features of the first through ninth methods. The tenth method includes a step of enumerating colonies of microorganisms that produce glucose oxidase.

An eleventh method is provided that can have all of the features of the first through tenth methods. The eleventh method includes a step of providing a chromogenic β-D-xylopyranosidase substrate in combination with the hydrogen peroxide indicating reagent, and a step of detecting a reaction of the chromogenic β-D-xylopyranosidase substrate.

A twelfth method is provided that can have all of the features of the eleventh method. The twelfth method includes a step of differentiating the microorganism by detecting a β-D-xylopyranosidase reaction with the chromogenic β-D-xylopyranosidase substrate.

A thirteenth method is provided that can have all of the features of the eleventh and twelfth methods. In the thirteenth method, the chromogenic β-D-xylopyranosidase substrate can be p-nitrophenyl-β-D-xylopyranoside (NXP).

A fourteenth method is provided that can have all of the features of the first through thirteenth methods. In the fourteenth method, the culture medium is agar.

The invention will be further illustrated by reference to the following non-limiting Examples. All parts and percentages are expressed as parts by weight unless otherwise indicated.

EXAMPLES

All parts, percentages, ratios, etc. in the examples are by weight, unless noted otherwise. All microorganism cultures were purchased from The American Type Culture Collection (ATCC; Manassas, Va.). Solvents and other reagents used were obtained from Sigma-Aldrich Chemical Company; Milwaukee, Wis. unless specified differently.

Materials

Sterilized DI water refers to 18 megaohm sterile deionized water obtained by using a MILLI-Q Gradient System from Millipore Corporation, Bedford, Mass.

Yeast and mold count plates are available as 3M PETRIFILM™ Yeast and Mold Count Plates from 3M Microbiology, 3M Center Bldg. 275-5W-05, St. Paul, Minn. 55144-1000, USA.

Examples 1-17 and Comparative Examples C1-C6

Including Liquid from Grapes

Stock reagent solutions were prepared as follows:
A0: 10 mL of pH 7.4 filter-sterilized phosphate-buffered saline (PBS)
B: 44 mg BCIP was dissolved in 2.4 mL of 0.1N NaOH, and then diluted to 10 mL with PBS to make a solution 4.4 mg/mL in BCIP
C: 11 mg 4-aminoantipyrine (4-AAP) dissolved in 5 mL PBS to make a solution 2.2 mg/mL in 4-AAP
F0: 10 mL of filter-sterilized 50 mM N-tris(hydroxymethyl) methyl-2-aminoethane sulfonic acid sodium salt (TES)
G: 33 mg 4-AAP dissolved in 15 mL TES to make a solution 2.2 mg/mL in 4-AAP
H: 11 mg 3-(N-ethyl-3-methylanilino)-2-hydroxypropane sulfonic acid (TOOS) dissolved in 10 mL TES to make a solution 1.1 mg/mL in TOOS These stock reagent solutions were then combined to make five further plate-hydrating solutions (resulting concentrations are given in parentheses):
D0: 5 mL each of A0 and B (2.2 mg/mL BCIP)
E0: 5 mL each of B and C (2.2 mg/mL BCIP, 1.1 mg/mL 4-AAP)
I0: 5 mL each of F0 and G (1.1 mg/mL 4-AAP)
J0: 5 mL each of G and H (1.1 mg/mL 4-AAP, 0.55 mg/mL TOOS)
K0: 5 mL each of G and H+110 mg p-nitro-β-D-xylopyranoside (NXP) (1.1 mg/mL 4-AAP, 0.55 mg/mL TOOS, 11 mg/mL NXP)

To each of solutions D0, E0, I0, J0 and K0 was added 20 μL of a 5 mg/mL horseradish peroxidase (HRP) solution to provide a concentration of HRP of about 10 μg/mL.

A sample of 100.8 g of red seedless grapes (bought at the local grocery store) was stomached twice at 235 rpm for 45 seconds on a Seward Stomacher 400 Circulator (from Seward Laboratory Systems Inc., Bohemia, N.Y.). A 5 mL sample of the resulting liquid (pH 4.2) was diluted to 50 mL with sterilized DI water, and then 1.1 mL was added to each of the solutions A0, D0, E0, F0, I0, J0 and K0 (including the added HRP) to make solutions A, D, E, F, I, J and K, respectively. The solutions are summarized in Table 1:

TABLE 1

| Solution | Buffer | BCIP (mg/mL) | 4-AAP (mg/mL) | TOOS (mg/mL) | NXP (mg/mL) |
|---|---|---|---|---|---|
| A (PBS control) | PBS | 0 | 0 | 0 | 0 |
| D (added BCIP) | PBS | 2 | 0 | 0 | 0 |
| E (added BCIP + 4-AAP) | PBS | 2 | 1 | 0 | 0 |
| F (TES control) | TES | 0 | 0 | 0 | 0 |
| I (4-AAP) | TES | 0 | 1 | 0 | 0 |
| J (4-AAP + TOOS) | TES | 0 | 1 | 0.5 | 0 |
| K (4-AAP + TOOS + NXP) | TES | 0 | 1 | 0.5 | 10 |

Five *Aspergillus* suspensions were prepared as follows: *Aspergillus niger* (ATCC#6275), *Aspergillus carbonarius* (ATCC#6277) and *Aspergillus brasiliensis* (ATCC#16404) were reconstituted from deep frozen stocks (−80° C.). The three organisms were diluted to $10^3$ organisms/mL with sterilized water. Two mixed solutions were also made: *A. carbonarius*+*A. niger* and *A. carbonarius*+*A. brasiliensis*. Each mixture contained $10^3$ organisms/mL ($5 \times 10^2$ organisms/mL for each organism).

To each of six 3M PETRIFILM™ Yeast and Mold Count Plates (available from 3M Company, St. Paul, Minn.) was added 1 mL of solution A. Similarly, six 3M PETRIFILM™ Yeast and Mold Count Plates were prepared for each of solutions D, E, F, I, J and K in Table 1 to give a total of 42 plates. For each set of six plates, five plates were inoculated with suspensions of *A. carbonarius, A. brasiliensis, A. niger, A. carbonius+A. niger* and *A. carbonarius+A. brasiliensis*, respectively. The sixth plate in each set was used as a control (no microorganisms added). Inoculation was performed by adding 50 μL of the particular reconstituted *Aspergillus* suspension (or mixed suspension) to 950 μL of the appropriate solution from Table 1 to make a 1 mL test suspension containing roughly 50 organisms. After inoculation, the plates were placed in an incubator set to 30° C. The plates were viewed at various intervals and the images were recorded on a standard Hewlett Packard SCANJET ADF document scanner (Hewlett Packard Company, Palo Alto, Calif.) and saved as JPEG files. Colony counts were determined by inspection. Colony counts for the single-species samples were tabulated in Tables 2-4 for *A. carbonarius, A. brasiliensis*, and *A. niger*, respectively.

TABLE 2

Colony counts for samples containing *A. carbonarius* and HRP.

| Example | Solution | 21 h | 24 h | 26 h | 42 h | 48 h | 72 h |
|---|---|---|---|---|---|---|---|
| C1 | A (PBS control) | 0 | 0 | 0 | 13 | 14 | 14 |
| 1 | D (added BCIP) | 12 | 13 | 13 | 14 | 15 | 14 |
| 2 | E (added BCIP + 4-AAP) | 19 | 22 | 22 | 20 | 20 | 21 |
| C2 | F (TES control) | 0 | 0 | 0 | 21 | 22 | 20 |
| 3 | I (4-AAP) | 19 | 19 | 19 | 19 | 19 | 19 |
| 4 | J (4-AAP + TOOS) | 16 | 17 | 16 | 17 | 17 | 17 |
| 5 | K (4-AAP + TOOS + NXP) | 12 | 17 | 17 | 16 | 15 | 17 |

The results in Table 2 show that, in the presence of grape juice, *A. carbonarius* can be detected within 24 hours by the addition of one of several glucose oxidase-sensitive reagents. Plates prepared with buffer solutions lacking these reagents (comparative examples C1 and C2) do not show visible colonies within 26 hours.

TABLE 3

Colony counts for samples containing *A. brasiliensis* and HRP.

| Example | Solution | 21 h | 24 h | 26 h | 42 h | 48 h | 72 h |
|---|---|---|---|---|---|---|---|
| C3 | A (PBS control) | 0 | 0 | 0 | 10 | 10 | 9 |
| 6 | D (added BCIP) | 0 | 9 | 9 | 9 | 11 | 11 |
| 7 | E (added BCIP + 4-AAP) | 1 | 5 | 10 | 16 | 15 | 15 |
| C4 | F (TES control) | 0 | 0 | 0 | 22 | 22 | 24 |
| 8 | I (4-AAP) | 18 | 18 | 18 | 18 | 18 | 18 |
| 9 | J (4-AAP + TOOS) | 22 | 22 | 21 | 19 | 20 | 22 |
| 10 | K (4-AAP + TOOS + NXP) | 31 | 38 | 40 | 41 | 38 | 42 |

The results in Table 3 show that, in the presence of grape juice, *A. brasiliensis* can be detected within 24 hours by the addition of one of several glucose oxidase-sensitive reagents. Plates prepared with buffer solutions lacking these reagents (comparative examples C3 and C4) do not show visible colonies within 26 hours.

TABLE 4

Colony counts for samples containing *A. niger* and HRP.

| Example | Solution | 21 h | 24 h | 26 h | 42 h | 48 h | 72 h |
|---|---|---|---|---|---|---|---|
| C5 | A (PBS) | 0 | 0 | 0 | 18 | 18 | 16 |
| 11 | D (added BCIP) | 0 | 18 | 18 | 18 | 21 | 20 |
| 12 | E (added BCIP + 4-AAP) | 0 | 2 | 7 | 10 | 11 | 10 |
| C6 | F (TES) | 0 | 0 | 0 | 11 | 11 | 15 |
| 13 | I (4-AAP) | 1 | 15 | 15 | 18 | 18 | 18 |
| 14 | J (4-AAP + TOOS) | 0 | 14 | 16 | 16 | 16 | 16 |
| 15 | K (4-AAP + TOOS + NXP) | 0 | 1 | 3 | 8 | 8 | 8 |

The results in Table 4 show that, in the presence of grape juice, *A. niger* can be detected in 24-26 hours by the addition of one of several glucose oxidase-sensitive reagents. Plates prepared with buffer solutions lacking these reagents (comparative examples C5 and C6) do not show visible colonies within 26 hours.

The results for all five *Aspergillus* suspensions and the control are shown in Table 5 for plates prepared with solution "I" (TES buffer, HRP/4-AAP indicating reagent). These results show that the addition of 4-AAP is advantageous for the early enumeration of all three of these organisms. The lack of false positives was demonstrated by the control sample, containing no added organisms, which was 0 at all time points.

TABLE 5

Colony counts with HRP/4-AAP indicating reagent (solution "I").

| Example | 21 h | 24 h | 26 h | 42 h | 48 h | 72 h |
|---|---|---|---|---|---|---|
| Control | 0 | 0 | 0 | 0 | 0 | 0 |
| 3 (*A. carbonarius*) | 19 | 19 | 19 | 19 | 19 | 19 |
| 8 (*A. brasiliensis*) | 18 | 18 | 18 | 18 | 18 | 18 |
| 13 (*A. niger*) | 1 | 15 | 15 | 18 | 18 | 18 |
| 16 (*A. carbonarius + A. niger*) | 7 | 16 | 16 | 18 | 18 | 18 |
| 17 (*A. carbonarius + A. brasiliensis*) | 7 | 7 | 7 | 7 | 7 | 7 |

Colonies resulting from the addition of 4-AAP alone were stained red at the 24 hour time point, and these colonies were also recognized by a 3M PETRIFILM™ PLATE READER device (PPR; available from 3M Company, St. Paul, Minn.), enabling automated counting. At later time points, an automated reading was less successful. A comparison of the 24 hour colony counts determined from direct (visual) observation and counts determined from the PPR is shown in Table 6.

TABLE 6

Colony counts at 24 hours, comparing direct (visual) observations in Table 5 vs. counts obtained with a plate reader device (PPR) for the same samples.

| Example | Direct (visual) observation | PPR |
|---|---|---|
| Control | 0 | 0 |
| 3 (*A. carbonarius*) | 19 | 29 |
| 8 (*A. brasiliensis*) | 18 | 19 |
| 13 (*A. niger*) | 15 | 17 |
| 16 (*A. carbonarius + A. niger*) | 16 | 20 |
| 17 (*A. carbonarius + A. brasiliensis*) | 7 | 13 |

The use of 4-AAP on the YM plates without other additional chromogenic substrates resulted in the formation of small red-stained colonies by all three organisms. In order to distinguish between them, more complex reagent mixtures were beneficial. For example, the 2 mg/mL BCIP solution (solution D, no 4-AAP) enabled ready discrimination of *A. brasiliensis* within 48 hours, giving small dark blue colonies with a black center and rim. *A. niger* and *A. carbonarius* colonies were both much paler than *A. brasiliensis*, *A. carbonarius* being smaller than *A. niger* and possessing a darker rim. Use of the 2 mg/mL of BCIP in combination with 1 mg/mL 4-AAP (solution E) enabled clear discrimination of all three species at 72 hours, *A. niger* colonies appearing as dark ovals with radiating blue hyphae, *A. brasiliensis* possessing prominent large red dendritic hyphal structures with a diffuse blue background, and *A. carbonarius* having red hyphae with minimal blue coloration (*A. carbonarius* colonies were also noted to have an irregular, ragged shape).

Examples 18-25 and Comparative Examples C7-C8

Four stock solutions were prepared as follows:
AA: 50 mM N-tris(hydroxymethyl)methyl-2-aminoethane sulfonic acid (TES)
XX: 2 mg/mL 4-aminoantipyrine (4-AAP) and 1 mg/mL 3-(N-ethyl-3-methylanilino)-2-hydroxypropane sulfonic acid (TOOS) in 50 mM TES
YY: 2 mg/mL 4-AAP in 50 mM TES
ZZ: 20 mg/mL p-nitrophenyl-β-D-xylopyranoside (NXP) in 50 mM TES.

The stock solutions were combined as follows to make five plate-hydrating solutions:
BB0: XX and AA were mixed together resulting in 1 mg/mL 4-AAP and 0.5 mg/mL TOOS in 50 mM TES
CC0: YY and AA were mixed together resulting in 1 mg/mL 4-AAP in 50 mM TES
DD: two ZZ solutions were mixed with two AA solutions resulting in 10 mg/mL NXP in 50 mM TES
EE0: XX and ZZ were mixed together resulting in 1 mg/mL 4-AAP, 0.5 mg/mL TOOS and 10 mg/mL NXP in 50 mM TES
FF0: YY and ZZ were mixed together resulting in 1 mg/mL 4-AAP and 10 mg/mL NXP in 50 mM TES An appropriate quantity of stock solution of 5 mg/mL HRP was added to solutions BB0, CC0, EE0 and FF0 to make the concentration of HRP in these samples 10 µg/mL. The samples with HRP are labeled BB, CC, EE and FF, respectively. These test solutions are summarized in Table 7.

TABLE 7

| Solution (in 50 mM TES buffer) | 4-AAP (mg/mL) | TOOS (mg/mL) | NXP (mg/mL) |
| --- | --- | --- | --- |
| AA (buffer alone) | 0 | 0 | 0 |
| BB (HRP + 4-AAP + TOOS) | 1 | 0.5 | 0 |
| CC (HRP + 4-AAP) | 1 | 0 | 0 |
| DD (NXP) | 0 | 0 | 10 |
| EE (HRP + 4-AAP + TOOS + NXP) | 1 | 0.5 | 10 |
| FF (HRP + 4-AAP + NXP) | 1 | 0 | 10 |

*A. carbonarius* (ATCC#6277), *A. brasiliensis* (ATCC#9642), *A. aculeatus* (ATCC#56925) *Penicillium amagasakiense* (ATCC#28686) and *A. flavus* (ATCC#9643) were reconstituted from deep frozen stocks (−80° C.). The five organisms were diluted to $10^3$ organisms/mL with sterilized DI water. Inoculation was performed by adding 50 µL of the particular reconstituted organism suspension to 950 µL of each of the test solutions BB-FF from Table 7 to make 1 mL test suspensions containing roughly 50 organisms each. Comparative examples used these same organisms, but were run with control solution AA. Plates were incubated at 28-30° C. and viewed and imaged at various time points. Results for the glucose oxidase producing organisms *A. carbonarius* and *A. brasiliensis* are summarized in Table 8.

TABLE 8

| Example | Organism | Solution | Time | Characteristics |
| --- | --- | --- | --- | --- |
| C7 | A. carbonarius | AA (buffer alone) | 41 h | Faint blue colonies |
| 18 | A. carbonarius | BB (HRP + 4-AAP + TOOS) | 24 h | Purple spots |
| 19 | A. carbonarius | CC (HRP + 4-AAP) | 24 h | Small red colonies |
| 20 | A. carbonarius | EE (HRP + 4-AAP + TOOS + NXP) | 24 h | Purple spots |
| 21 | A. carbonarius | FF (HRP + 4-AAP + NXP) | 24 h | Small red colonies |
| C8 | A. brasiliensis | AA (buffer alone) | 41 h | Faint blue colonies |
| 22 | A. brasiliensis | BB (HRP + 4-AAP + TOOS) | 24 h | Purple spots |
| 23 | A. brasiliensis | CC (HRP + 4-AAP) | 24 h | Small red colonies |
| 24 | A. brasiliensis | EE (HRP + 4-AAP + TOOS + NXP) | 24 h | Purple spots |
| 25 | A. brasiliensis | FF (HRP + 4-AAP + NXP) | 24 h | Small red colonies |

*A. carbonarius* and *A. brasiliensis* both yielded purple spots with solutions BB (4-AAP+TOOS) and EE, and small red colonies with solutions CC and FF at 24 hours. None of the other organisms produced visible colonies at this time. Faint blue colonies appeared in the comparative examples C7 and C8 that used control solution AA for *A. carbonarius* and *A. brasiliensis* between 41 and 48 hours. Similarly, the glucose oxidase-producing organism *P. amagasakiense* began to show purple spots in solutions BB and EE, red colonies in solution CC and FF at 32 hours, and colonies only began to appear with solutions AA and DD between 47 and 66 hours. This demonstrated early detection of organisms that produce glucose oxidase.

Conversely, *A. aculeatus* colonies began to appear at 41 hours in all six solutions, and *A. flavus* at 47 hours. Although the color varied somewhat with reagent solution (plum-colored in the presence of 4-AAP and blue/green in its absence), the morphology and growth rate of these colonies was largely independent of solution. This demonstrated that colonies that do not produce glucose oxidase are detected no earlier in the presence of these reagents than in their absence.

Colonies of *A. brasiliensis* and *A. carbonarius* were difficult to distinguish reliably from each other even at 48 hours. However, with additional time, the purple spots that developed with solutions BB and EE gradually spread out and faded leaving a small center. With solution DD (NXP), this center was red in both cases, but for solution EE (4-AAP/TOOS/NXP) *A. carbonarius* yielded a red center and *A. brasiliensis* a dark purple one. Thus, with additional time, closely related glucose oxidase-generating organisms could still be distinguished by the additional use of a substrate to β-D-xylopyranosidase.

Examples 26 and 27

Comparison of Organisms Reported to Produce Ochratoxin A

Isolates of two organisms reported to produce Ochratoxin A were tested: *A. ochraceus* (ATCC#22947) and *A. tubingen-* sis (ATCC#76608). *A. tubingensis* is a subset of *Aspergillus* section *Nigri*, closely related to *A. niger* and *A. carbonarius*, and may be involved in the infection of wine grapes in Italy (Appl. Environ. Microbiology, 72, 680-685 (2006)). Two other organisms were also tested: *A. brasiliensis* (ATCC#9642) and *A. japonicus* (ATCC#52036). *A. japonicus* is neither glucose oxidase-producing nor ochratoxin A-producing, but is reported to infect grapes.

The four organisms were diluted to $10^3$ organisms/mL with sterilized DI water. Two plates for each organism were prepared with 50 mM TES buffer (for comparative examples, TES in Table 9), and two with 1.0 mg/mL 4-AAP/0.5 mg/mL TOOS/10 µg/mL HRP in 50 mM TES buffer (4-AAP/TOOS in Table 9). Inoculation was performed by adding 50 µL of the particular reconstituted organism suspension to 950 µL of either TES or 4-AAP/TOOS solution to make 1 mL test suspensions containing roughly 50 organisms each. Plates were incubated at 28-30° C. and viewed and imaged at various time points. Colony counts (average of two plates) at various time points are shown in Table 9.

TABLE 9

Colony counts, contrasting the ochratoxin-producing (but non-glucose oxidase-producing) *A. ochraceus* with the glucose oxidase-producing organisms *A. brasiliensis* and *A. tubingensis*. *A. japonicus*, which produces neither, is included for comparison.

| Time | *A. japonicus* TES | *A. japonicus* 4-AAP/TOOS | *A. brasiliensis* (Ex. 26) TES | *A. brasiliensis* (Ex. 26) 4-AAP/TOOS | *A. ochraceus* TES | *A. ochraceus* 4-AAP/TOOS | *A. tubingensis* (Ex. 27) TES | *A. tubingensis* (Ex. 27) 4-AAP/TOOS |
|---|---|---|---|---|---|---|---|---|
| 23 h | 0 | 0 | 0 | 11 | 0 | 0 | 0 | 15 |
| 27 h | 0 | 0 | 0 | 21 | 0 | 0 | 0 | 18 |
| 32 h | 0 | 0 | 0 | 22 | 0 | 0 | 0 | 18 |
| 37 h | 0 | 0 | 0 | 21 | 0 | 0 | 1 | 18 |
| 47 h | 18 | 21 | 12 | 22 | 0 | 0 | 26 | 19 |
| 54 h | 25 | 23 | 12 | 22 | 0 | 2 | 25 | 18 |
| 58 h | 26 | 24 | 12 | 21 | 4 | 4 | 25 | 19 |
| 71 h | 26 | 24 | 12 | 19 | 6 | 6 | 25 | 19 |
| 78 h | 26 | 24 | 11 | 18 | 6 | 6 | 24 | 19 |
| 96 h | 25 | 23 | 11 | 19 | 6 | 6 | 24 | 19 |

Two of the organisms (*A. brasiliensis*, and *A. tubingensis*), produced colored spots earlier in the presence of TOOS/4-AAP than in their absence (by about 24 hours). Colonies of the mold *A. ochraceus*, which produces ochratoxin A but not glucose oxidase, appeared at approximately the same time irrespective of the presence or absence of TOOS/4-AAP, as did colonies of *A. japonicus*. This demonstrated early detection of organisms that produce glucose oxidase.

Examples 28-32

Lower Temperature Incubation and Detection

Isolates of five organisms known to generate glucose oxidase were tested: *A. carbonarius* (Example 28), *A. brasiliensis* (Example 29), *A. tubingensis* (ATCC#76608; Example 30), *P. amagasakiense* (ATCC#28686; Example 31), and *P. funiculosum* (ATCC #11797; Example 32). Deep-frozen (−80° C.) stocks of each organism were diluted to $10^3$ organisms/mL with a sterile saline (145 nM NaCl) suspension. Three reagent solutions were prepared: 50 mmol TES buffer (TES in Table 10), 0.5 mg/mL TOOS/1.0 mg/mL 4-AAP/10 µg/mL HRP in 50 mmol TES (4-AAP/TOOS in Table 10), and 1.0 mg/mL 4-AAP/10 µg/mL HRP in 50 mmol TES (4-AAP in Table 10). Example numbers are labeled as in previous examples. Three plates were prepared for each organism by taking 50 µL of these dilutions and adding them to 950 µL of the test solution to make a 1 mL test solutions containing roughly 50 organisms. Plates were incubated at room temperature and viewed and imaged at various time points. A thermocouple inserted into the stack of plates consistently measured the temperature over the entire incubation at 19-20° C. Colony counts at the indicated time points are shown in Table 10.

TABLE 10

Colony counts from lower temperature (19-20° C.) incubations.

| Time | *A. carbonarius* (Ex. 28) TES | *A. carbonarius* (Ex. 28) 4-AAP/TOOS | *A. carbonarius* (Ex. 28) 4-AAP | *A. brasiliensis* (Ex. 29) TES | *A. brasiliensis* (Ex. 29) 4-AAP/TOOS | *A. brasiliensis* (Ex. 29) 4-AAP | *A. tubingensis* (Ex. 30) TES | *A. tubingensis* (Ex. 30) 4-AAP/TOOS | *A. tubingensis* (Ex. 30) 4-AAP | *P. amagasakiense* (Ex. 31) TES | *P. amagasakiense* (Ex. 31) 4-AAP/TOOS | *P. amagasakiense* (Ex. 31) 4-AAP | *P. funiculosum* (Ex. 32) TES | *P. funiculosum* (Ex. 32) 4-AAP/TOOS | *P. funiculosum* (Ex. 32) 4-AAP |
|---|---|---|---|---|---|---|---|---|---|---|---|---|---|---|---|
| 6 h | 0 | 0 | 0 | 0 | 0 | 0 | 0 | 0 | 0 | 0 | 0 | 0 | 0 | 0 | 0 |
| 19 h | 0 | 0 | 0 | 0 | 0 | 0 | 0 | 0 | 0 | 0 | 0 | 0 | 0 | 0 | 0 |
| 25 h | 0 | 0 | 0 | 0 | 0 | 0 | 0 | 0 | 0 | 0 | 0 | 0 | 0 | 0 | 0 |
| 29 h | 0 | 0 | 0 | 0 | 0 | 0 | 0 | 0 | 0 | 0 | 0 | 0 | 0 | 0 | 0 |
| 33 h | 0 | 0 | 0 | 0 | 0 | 0 | 0 | 2 | 1 | 0 | 0 | 0 | 0 | 0 | 0 |
| 45 h | 0 | 20 | 14 | 0 | 12 | 12 | 0 | 14 | 20 | 0 | 0 | 0 | 0 | 0 | 0 |
| 48 h | 0 | 20 | 17 | 0 | 12 | 12 | 0 | 14 | 20 | 0 | 0 | 0 | 0 | 0 | 0 |
| 53 h | 0 | 22 | 15 | 0 | 20 | 18 | 0 | 15 | 21 | 0 | 0 | 0 | 0 | 1 | 0 |
| 55.5 h | 0 | 23 | 20 | 0 | 19 | 18 | 0 | 15 | 21 | 0 | 0 | 0 | 0 | 2 | 0 |
| 69.5 h | 0 | 23 | 17 | 0 | 18 | 19 | 1 | 15 | 20 | 0 | 13 | 6 | 0 | 21 | 14 |
| 99.5 h | 17 | 23 | 19 | 19 | 21 | 19 | 16 | 15 | 21 | 0 | 21 | 26 | 0 | 16 | 16 |
| 118 h | 19 | 23 | 17 | 19 | 21 | 19 | 15 | 15 | 21 | 29 | 23 | 26 | 14 | 20 | 16 |
| 142 h | 18 | 23 | 16 | 19 | 20 | 19 | 15 | 15 | 20 | 29 | 24 | 26 | 14 | 20 | 16 |
| 166 h | 18 | 24 | 16 | 20 | 21 | 19 | 17 | 15 | 20 | 29 | 24 | 25 | 14 | 20 | 16 |

It is apparent from the data in Table 10 that the growth rate of the organisms was significantly retarded at 19-20° C. in comparison to the growth rates at 28-30° C. in the prior examples. With the added hydrogen peroxide indicating reagents, however, the *Aspergillus* colonies appear in 2 days rather than 4 days in their absence. Colonies of the two glucose oxidase-producing *Penicillium* species showed up in 3 days with the reagent solutions rather than in 5 days in their absence. This data demonstrated a reduction in time-to-detection at lower incubation temperatures (19-20° C., where the organisms grow more slowly than at 30° C.), due to addition of glucose-oxidase sensing reagents.

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

What is claimed is:

1. A method of distinguishing one or more of *Aspergillus niger, Aspergillus carbonarius, Aspergillus brasiliensis, Aspergillus tubingensis, Penicillium amagasakiense*, and *Penicillium funiculosum* from one another, from one or more other microorganisms or both comprising:

providing
- a thin film culture device comprising a cold-water-soluble gelling agent,
- a culture medium to support growth of a microorganism that produces glucose oxidase, wherein the culture medium comprises dextrose,
- a hydrogen peroxide indicating reagent comprising horseradish peroxidase and a first chromogenic substrate comprising 4-aminoantipyrene, 3-(N-ethyl-3-methylanilino)-2-hydroxypropanesulfonic acid sodium salt, or a combination thereof,
- a second chromogenic substrate comprising 5-bromo-4-chloro-3-indolyl-phosphate, a chromogenic β-D-xylopyranosidase substrate, or a combination thereof, and
- a sample suspected of containing the microorganism;

combining, in the culture device, a predetermined volume of the sample, the culture medium, and hydrogen peroxide indicating reagent and the second chromogenic substrate;

incubating the culture device;

detecting a reaction of both the first chromogenic substrate and the second chromogenic substrate; and distinguishing the microorganisms based upon differences in one or more of color, shape, size and time period detected from the reaction of both the first chromogenic substrate and the second chromogenic substrate.

2. The method of claim 1, wherein the thin film culture device comprises the culture medium.

3. A method of differentiating one or more of *Aspergillus niger, Aspergillus carbonarius, Aspergillus brasiliensis, Aspergillus tubingensis, Penicillium amagasakiense*, and *Penicillium funiculosum* from one another, from one or more other microorganisms or both comprising:

providing
- a thin film culture device comprising a cold-water-soluble gelling agent,
- a culture medium to support growth of a microorganism that produces glucose oxidase, wherein the culture medium comprises dextrose,
- a hydrogen peroxide indicating reagent comprising horseradish peroxidase and a first chromogenic substrate comprising 4-aminoantipyrene, 3-(N-ethyl-3-methylanilino)-2-hydroxypropanesulfonic acid sodium salt, or a combination thereof, and
- a second chromogenic substrate comprising 5-bromo-4-chloro-3-indolyl-phosphate, a chromogenic β-D-xylopyranosidase substrate, or a combination thereof,
- and a sample suspected of containing the microorganism;

combining a predetermined volume of sample and the culture medium to form a first mixture;

combining, in the culture device, the first mixture, the hydrogen peroxide indicating reagent, and the second chromogenic substrate;

incubating the culture device; and detecting a reaction of both the first chromogenic substrate and the second chromogenic substrate, wherein distinguishing the microorganisms based upon differences in one or more of color, shape, size and time period detected from the reaction of both the first chromogenic substrate and the second chromogenic substrate.

4. The method of claim 3, wherein the first mixture is incubated prior to being combined with the hydrogen peroxide indicating reagent.

5. The method of any one of the previous claims, wherein incubating the culture device comprises incubating the culture device aerobically.

6. The method of claim 1, wherein the reaction of the first chromogenic substrate and the second chromogenic substrate are differentiable within 48 hours of the start of incubating the culture device.

7. The method of claim 1, wherein the reaction of the first chromogenic substrate and the second chromogenic substrate are differentiable within 24 hours of the start of incubating the culture device.

8. The method of claim 1, wherein the first chromogenic substrate comprises 4-aminoantipyrine and the second chromogenic substrate comprises 5-bromo-4-chloro-3-indolyl phosphate.

9. The method of claim 8, wherein the first chromogenic substrate further comprises 3-(N-ethyl-3-methylanilino)-2-hydroxypropanesulfonic acid sodium salt.

10. The method of claim 1, wherein the second chromogenic substrate comprises both 5-bromo-4-chloro-3-indolyl-phosphate and the chromogenic β-D-xylopyranosidase substrate.

11. The method of claim 10, wherein the chromogenic β-D-xylopyranosidase substrate comprises at least one of p-nitrophenyl-β-D-xylopyranoside or o-nitrophenyl-β-D-xylopyranoside.

12. The method of claim 1, wherein *Aspergillus niger, Aspergillus carbonarius*, and *Aspergillus brasiliensis* can be detected and distinguished from each other at 72 hours.

* * * * *